(12) United States Patent
Hara et al.

(10) Patent No.: US 6,248,346 B1
(45) Date of Patent: *Jun. 19, 2001

(54) CHEWING GUM AND PRODUCTION OF THE SAME

(75) Inventors: Yukihiko Hara, Fujieda; Mikio Nakayama, Narashino, both of (JP)

(73) Assignee: Mitsui Norin Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/039,953

(22) Filed: Mar. 16, 1998

(30) Foreign Application Priority Data

Mar. 18, 1997 (JP) .................................................. 9-083388

(51) Int. Cl.⁷ ................................ A61K 9/68; A61K 7/26
(52) U.S. Cl. .............................. 424/440; 424/48; 424/58; 424/401; 424/409; 424/410; 424/419; 424/439; 424/458
(58) Field of Search .................................... 424/440, 439, 424/441, 409, 410, 419, 48, 58

(56) References Cited

U.S. PATENT DOCUMENTS 5,137,922 * 8/1992 Shimamura et al. .
5,409,692 * 4/1995 Nakahara ................................ 424/49
5,487,902 * 1/1996 Anderson et al. .

FOREIGN PATENT DOCUMENTS

3297352 * 12/1991 (JP) .

OTHER PUBLICATIONS

Hara and Ishigami, Gum base conatining tea polyphenols and collagens, AN 1992: 150473, CAPLUS abstract, Dec. 27, 1991.*

Roedig–Penman, et al , Antioxidant properties of Catechins and Green Tea Extracts in Model Food Emulsions, AN 1997:657645, CAPLUS abstract, 1997.*

* cited by examiner

Primary Examiner—James O. Wilson
(74) Attorney, Agent, or Firm—Frishauf, Holtz, Goodman, Langer & Chick, P.C.

(57) ABSTRACT

A chewing gum which has a preventative effect against infection by influenza virus and inhibits dissemination of influenza virus. The chewing gum comprises adding at least 0.03 weight % of at least one tea polyphenol, for a chewing gum containing no organic acids; the chewing gum comprises at least 0.01 weight % of at least one tea polyphenol for a chewing gum containing at least one organic acid.

4 Claims, No Drawings

CHEWING GUM AND PRODUCTION OF THE SAME

FIELD OF THE INVENTION

The present invention relates to a chewing gum and a method of producing the same. More specifically, a chewing gum having an inhibitory action against influenza virus and a method of producing said chewing gum, to which a specific amount of tea polyphenols is added.

BACKGROUND OF THE INVENTION

Chewing gum has an effect of refreshing one's mount, so many people enjoy it, and there are a variety of flavors, including the sugarless types, on the market. However, up until now there has not been on the market a chewing gum which has a preventative action against infection to influenza virus.

A purpose of the present invention is to provide a chewing gum which has a preventative reaction against infection by influenza virus, and inhibits the spread of said viruses.

SUMMARY OF THE INVENTION

First, the present invention relates to a chewing gum characterized by including 0.03 weight % or more of tea polyphenol in a chewing gum containing no organic acids.

Second, the present invention relates to a method of producing a chewing gum which comprises adding 0.03 weight % or more of tea polyphenol to a chewing gum containing no organic acids.

Third, the present invention relates to a chewing gum characterized by including 0.01 weight % or more of tea polyphenol in a chewing gum containing organic acids.

Finally, the present invention relates to a method of producing a chewing gum which comprises adding 0.01 weight % or more of tea polyphenol to a chewing gum containing organic acids.

Further, the present invention provides a method of preventing against infection by influenza virus which comprises administering an effective amount of tea polyphenols to a person through chewing a chewing gum mentioned above.

DETAILED DESCRIPTION OF THE PREFERRED EMBODIMENTS

The chewing gum of the present invention has as its special characteristic the addition of 0.03 weight % or more of tea polyphenols (0.01 weight % or more of tea polyphenols in the case where organic acids are contained in the chewing gum) to an ordinary chewing gum, and the production thereof should be carried out by the usual methods. That is to say, basically it can be produced by addition a specified amount of tea polyphenols to a gum base, mixing and shaping; but usually, regular components such as sugar, flavor, etc. are also optionally added. With the addition of an organic acid such as citric acid, malic acid, tartaric acid or fumaric acid, tea polyphenols are stabilized and the amount eluted in the mouth is increased when chewed, and thus such an addition of the organic acid is desirable.

The tea polyphenols used in the present invention are tea catechins are represented by general formula I below and theaflavins as represented by general formula II below, and these may be used singly or in combination.

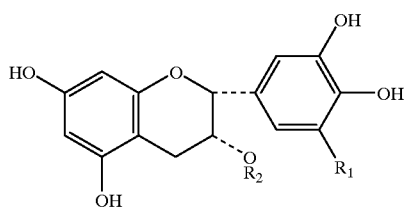

where $R_1$ is H or OH and $R_2$ is H or

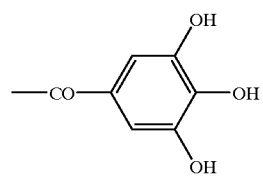

and

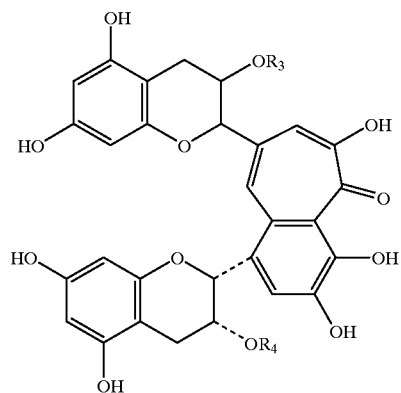

wherein $R_3$ and $R_4$ are H or

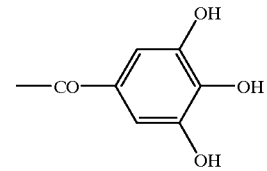

and $R_3$ and $R_4$ may be either the same or different to each other.

Specific examples of tea catechins as shown in general formula I above are as follows:

Epicatechin(EC): in general formula I $R_1$=H, $R_2$=H)

Epigallocatechin (EGC): in general formula I $R_1$=OH, $R_2$=H)

Epicatechin gallate (ECg): in general formula I $R_1$=H, $R_2$=

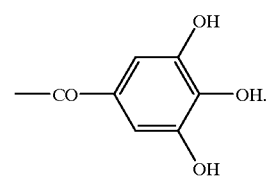

Epigallocatechin gallate (EGCg): in general formula 1, $R_1$=OH, $R_2$=

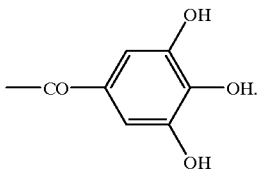

Out of these the preferable tea catechin contains at least one of the following: epigallocatechin, epicatechin gallate and epigallocatechin gallate. Particularly preferable is to use a tea catechin product which contains epigallocatechin gallate as the main component. For example Polyphenon 100™ (manufactured by Mitsui Norin Co. Ltd., Composition: (+) gallocatechin 1.44% (−) epicatechin 5.81%, (−) epigallocatechin 17.57% (−) epicatechin gallate 12.51% (−) epigallocatechin gallate 53.9%) or Polyphenon E™ (manufactured by Mitsui Norin Co. Ltd., Composition: (−) epicatechin 8.0% (−) epigallocatechin 18.0% (−) epicatechin gallate 2.5%. (−) epigallocatechin gallate 55.5%).

Specific examples of theaflavins as shown in the above general formula II are as follows:

Free theaflavin (TF1): in general formula II $R_3$=H, $R_4$=H.

Theaflavin monogallate A (TF2A): in general formula II, $R_3$=

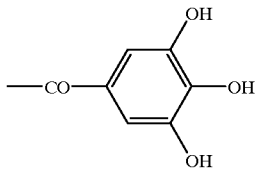

$R_4$=H.

Theaflavin monogallate B (TF2B): in general formula II, $R_3$=H, $R_4$=

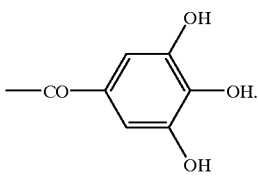

Theaflavin digallate (TF3): in general formula II $R_3$, $R_4$=

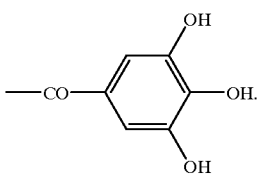

Among them, the preferable theaflavin contains theaflavin digallate as the main component, for example Polyphenon TF™ (manufactured by Mitsui Norin Co. Ltd., Composition: theaflavin 16.8%, theaflavin monogallate A 19.5%, theaflavin monogallate B 16.1%, theaflavin digallate 31.4%).

The above tea polyphenol products contain EGCg or ECg as their main component and may be produced using tea leaves as the raw material. The method for production is described in U.S. Pat. No. 4,673,530 (Japanese Patent Kokai 59-219384). U.S. Pat. No. 4,613,672 (Japanese Patent Kokai 60-13780) and Japanese Patent Kokai 61-130285 etc. The entire contents of U.S. Pat. No. 4,673,530 and U.S. Pat. No. 4,613,672 are hereby incorporated by reference. For example, there is a method whereby tea leaves are extracted in hot water, or a solvent selected from the group consisting of methanol, aqueous ethanol and aqueous acetone; then after the extract solution thus obtained is dissolved by mixing in an organic solvent, the organic solvent is evaporated to remove the same. Moreover, the concentrated solution of the extracted component obtained in this way may be subjected to high pressure liquid chromatography for separation into the individual components as described above.

Any kind of tea leaves may be used, for example apart from fresh tea leaves, unfermented tea, semi-fermented tea, green tea, instant green tea and even tea dregs may be used. About 10 weight % tea catechin is usually contained in tea leaves, and theaflavins are contained in black tea.

As for the amount of tea polyphenol to be added to the chewing gum, not all of the tea polyphenol contained in the gum is released when the gum is chewed, so the amount to be added should be calculated by taking the amount released (or eluted) in the mouth as a standard. If more than 2 ppm of tea polyphenols are present in the saliva as mentioned later, infection by the influenza virus will be inhibited, and the dissemination of said viruses will be prevented. The least amount of polyphenol in the saliva required to inhibit infection by and dissemination of such viruses is 2 ppm, or more preferably 2–10 ppm of tea polyphenols should be present in the saliva.

We investigated the amount of tea polyphenol which is released (or eluted) in the mouth when the chewing gum is chewed and found that as shown in Test Examples below, it was about 10 weight % in the case where no organic acids such as citric acid were present, and about 35 weight % in the case where organic acids were present.

Normally humans secrete about 1 ml of saliva per minute but when gum is chewed the amount secreted increased to about 3 ml per minute. When, for example, 3.2 g stick gum is chewed for 15 minutes, assuming that the elution of the polyphenol and secretion of the saliva during this time proceeds at a regular rate, the tea polyphenol should be added to the chewing gum in such an amount that more than 2 ppm tea polyphenols are contained in about 50 ml saliva.

Therefore, on consideration of the amount of tea polyphenol eluted from the above described chewing gum, the amount of tea polyphenol to be added to the chewing gum was calculated to be more than 0.03 weight %, preferably 0.5 to 2 weight % in the case where no organic acids are present and more than 0.01 weight %, preferably 0.2 to 1.5 weight % in the presence of organic acids.

The present invention provides a chewing gum which inhibits infectivity of the influenza virus by the addition of tea polyphenols, and inhibits the dissemination (or propagation) of said virus.

An example of a chewing gum composition for use in the present invention is as follows:

| Components | Weight % |
|---|---|
| gum base | 18–30% |
| sucrose | 50–70% |
| glucose | 5–10% |

-continued

| Components | Weight % |
|---|---|
| corn syrup | 5–20% |
| flavoring | 1–2% |
| others (organic acids/ polyphenol etc.) | 0–6% |

EXAMPLES

The present invention will be explained in more detail by way of the following examples Example 1

1.9 weight % tea catechin (Trade name: Polyphenon E™, manufactured by Mitsui Norin Co. Ltd.) was added to 98.1 weight % gum base and mixed well to produce stick gum (weight 3.2 g). Sweeteners and flavorings may be added as desired.

Example 2

1.9 wt. % tea catechin (Trade name: Polyphenon E™, manufactured by Mitsui Norin Co. Ltd.) and 1.0 wt. % citric acid were added to 97.1 wt. % gum base and mixed well to produce stick gum (weight 3.2 g).

Test Example 1

The chewing gums obtained in Examples 1 and 2 were broken into small pieces and added to 50 ml purified water and agitated for two hours. Then the chewing gum was removed and the solution was passed through a 0.45μ filter. To determine the amount of tea polyphenols contained in the gum extract solution obtained, the said solution was subjected to high pressure liquid chromatography (HPLC). Results are shown in Table 1. In Table 1, EGC is (−) epigallocatechin. EC is (−) epicatechin, EGCg is (−) epigallocatechin gallate, ECg is (−) epicatechin gallate.

TABLE 1

| Sample | EGC | EC | EGCg | ECg | TOTAL |
|---|---|---|---|---|---|
| Example 1 | 0 | 71 | 0 | 22 | 93 |
| Example 2 | 40 | 81 | 201 | 33 | 355 |
| Blank | 0 | 0 | 0 | 0 | 0 |

Remark: unit of the numerical value is ppm.

Text Example 2

Dilutions of the two gum extract solutions obtained as in Test Example 1 were used to examine prevention against infection by the influenza virus and inhibition of propagation of said virus. Viral infectivity was determined by plaque assay using MDCK cells (Madin-Darby canine kidney cells).

The 20x dilutions of samples from Example 1 and 2 were further diluted to make 40x, 80x, 160x, 320x dilutions. Equal amounts of solutions containing the virus (Influenza virus Type B, B/Bangkok/163/90) were added to the respective dilution samples to make the concentrations up to 200 pfu/100 μl and cultured in MEM medium for 10 minutes at 37° C. then monolayered MDCK cells were inoculated with the respective samples.

After absorption of the virus, 1% agar culture was spread over the petri dishes and after culturing for 96 hours at 34° C. in a 5% $CO_2$ incubator, 10% formaldehyde was added. Then they were colored with methylene blue and the plaque formed was counted. As a control a blank solution (1x dilution) was treated in the same way. In place of the sample solution, the same amount of MEM medium with the addition of the virus was used as a control to determine the number of plaque and form these control groups the average number of plaque was determined and this was used to calculate the plaque inhibition rate of the sample groups. Results are shown in Table 2.

As is clear from Table 2, the 80x dilution sample solution of Example 1, containing 1.2 ppm catechin, and the 160x dilution sample solution of Example 2, containing 2.2 ppm catechin almost completely inhibited the formation of plaque by viruses. Viral plaque formation was stable with the blank solution, showing the inhibitory effect of viral infectivity which resulted from the addition of tea catechin is reliable.

TABLE 2

| Sample | Dilution rate of sample | | | | |
|---|---|---|---|---|---|
| Example 1 | 20x | 40x | 80x | 160x | 320x |
| Number of plaque | 0, 0 | 0, 0 | 1, 2 | 52, 35 | 74, 80 |
| Plaque inhibition rate (%) | 100 | 100 | 98.3 | 48.0 | 13.2 |
| Example 2 | 20x | 40x | 80x | 160x | 320x |
| Number of plaque | 0, 0 | 0, 0 | 0, 0 | 1, 1 | 26, 23 |
| Plaque inhibition rate (%) | 100 | 100 | 100 | 98.9 | 73.5 |
| Blank | 1x | | | | |
| Number of plaque | 90, 100 | | | | |
| Plaque inhibition rate (%) | 0 | | | | |
| Virus control: | 87, 95, 96, 85, 84, 93, 92, 92, 95, 95, 99, 93 | | | | |
| | n = 12    P > 0.95 | | | | |

Test Example 3

This experiment was conducted with respect to a sample solution of Example 1 in the same way as in Test Example 2 using Influenza virus Hong Kong Type A/Kita Kyushu/159/93 (H3N2). Results are shown in Table 3.

As in evident from Table 3, the 40x dilution sample solution of Example 1 containing 2.3 ppm tea catechins almost completely inhibited the formation of viral plaque.

TABLE 3

| Sample | Dilution rate of sample | | | | |
|---|---|---|---|---|---|
| Example 1 | 20x | 40x | 80x | 160x | 320x |
| Number of plaque | 0, 0 | 1, 1 | 12, 11 | 51, 51 | 78, 73 |
| Plaque inhibition rate (%) | 100 | 99.1 | 89.4 | 52.9 | 32.7 |
| Blank | 1x | | | | |
| Number of plaque | 90, 100 | | | | |
| Plaque inhibition rate (%) | 0 | | | | |
| Virus control: | 105, 102, 114, 110, 115, 112, 94, 107, 116, 107 | | | | |
| | n = 10    0, 95 > P > 0.90 | | | | |

The entire disclosure of Japanese Patent application No. 9-83388 filed on Mar. 18, 1997 including specification, claims and summary are incorporated herein by reference in its entirety.

What is claimed is:

1. A method for inhibiting infection by influenza virus and inhibiting dissemination of influenza virus which comprises administering to a person in need thereof a chewing gum containing at least 0.01 weight % of eqigallocatechin gallate in a mixture of tea polyphenols, and at least one organic acid in an amount up to 6 weight % to elute 2 ppm to 10 ppm of said epigallocatechin gallate into the saliva of said person during chewing of the gum.

2. The method of claim 1, wherein the at least one organic acid is selected from the group consisting of citric acid, malic acid, tartaric acid or fumaric acid.

3. The method of claim 2, wherein the mixture of tea polyphenols is in an amount of 0.2 to 1.5 weight %.

4. The method of claim 1, wherein the at least one organic acid is citric acid.

* * * * *